(12) United States Patent
Soluri et al.

(10) Patent No.: US 6,242,744 B1
(45) Date of Patent: Jun. 5, 2001

(54) MINIATURIZED GAMMA CAMERA WITH VERY HIGH SPATIAL RESOLUTION

(75) Inventors: Alessandro Soluri; Roberto Pani, both of Rome (IT)

(73) Assignee: C.N.R. Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 09/202,894
(22) PCT Filed: Apr. 22, 1998
(86) PCT No.: PCT/IT98/00096
§ 371 Date: Dec. 22, 1998
§ 102(e) Date: Dec. 22, 1998
(87) PCT Pub. No.: WO98/48300
PCT Pub. Date: Oct. 29, 1998

(30) Foreign Application Priority Data

Apr. 23, 1997 (IT) .............................. RM97A0233

(51) Int. Cl.$^7$ .......................... G01T 1/161; G01T 1/208
(52) U.S. Cl. ................................ 250/363.1; 250/363.02; 250/367
(58) Field of Search ........................... 250/363.1, 363.02, 250/367, 366

(56) References Cited

U.S. PATENT DOCUMENTS

| 5,783,829 | * | 7/1998 | Sealock et al. ....................... 250/367 |
| 5,864,141 | * | 1/1999 | Majewski et al. ............... 250/363.02 |
| 6,021,341 | * | 2/2000 | Scibilia et al. ....................... 600/405 |

FOREIGN PATENT DOCUMENTS

WO 96/37791 * 11/1996 (WO).
9703369  1/1997 (WO).

* cited by examiner

Primary Examiner—Constantine Hannaher
Assistant Examiner—Otilia Gabor
(74) Attorney, Agent, or Firm—Browdy and Neimark

(57) ABSTRACT

The miniaturized gamma camera has all specific functionalities of gamma cameras, with extremely high spatial resolution (about 1–2 mm) and dimensions of about 22 mm×22 mm of active area and total size of about 35 mm×35 mm, such as to fit in one of the surgeon's hands and to be handled with absolute ease.

8 Claims, 6 Drawing Sheets

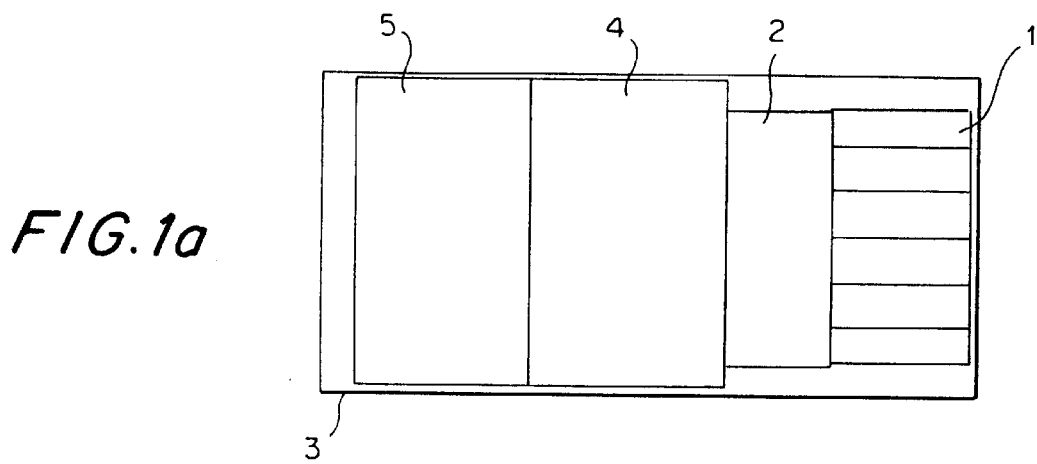
FIG.1a
FIG.2
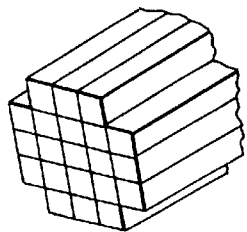
FIG.3
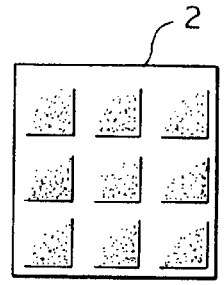
FIG.4
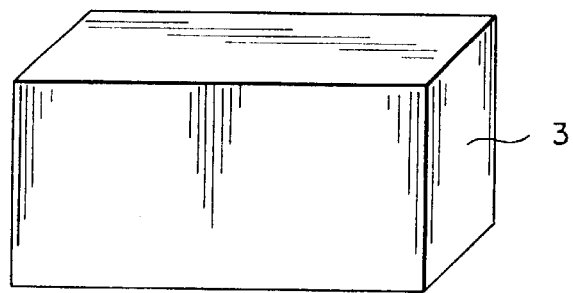

MINIATURIZED GAMMA CAMERA WITH VERY HIGH SPATIAL RESOLUTION

The invention relates to a miniaturized gamma camera with high spatial resolution for the localization of tumours, for external diagnostic use or to be utilized during surgical operations.

It is well known that in order to remove a tumour surgically, the surgeon needs to localize it and for that purpose he/she normally uses the results obtained with the diagnostic systems employed to identify the tumour itself (radiography, CAT-scans, NMR, scintigraphy).

However, at the time of surgery, after "opening" the part, the surgeon may still need to localize better the point to be cut and removed and, therefore, he/she may be aided by a so-called "surgical probe": after injecting into the patient a radio pharmaceutical product that has the peculiarity of attaching itself preferentially in tumour cells, he/she detects the gamma radiations emitted by the radioisotope, present in the molecules of the pharmaceutical product, by means of a probe of the type of a GEIGER-MULLER counter.

The probe is sensitive to gamma radiation in such a way as to give analogue signals proportional to the radioisotope concentration detected. The detected signals are converted into digital signals providing a luminous or acoustic scale proportional to the intensity of the signal. The limit is constituted by the impossibility of providing an image in real time but only the display of the count on areas of interest.

Gamma cameras currently in existence often have very large areas and are not easily handled during surgical interventions in the course of the operations. For this purpose, therefore, surgical probes are alternatively used that are able to localize the tumours but unable to display the receiving areas and hence to effect an imaging to describe the situation under examination.

For example, if a peritumoral lymph node is enlarged and anti CEA antibodies have been injected before the intervention, the probe is placed close to the lymph node: if radioactivity is intense, then the lymph node is clearly invaded by neoplastic cells expressing CEA. Last generation probes (CNR patent No. RM95A000451 of Jul. 13, 1995 and corresponding EPO patent application no. 96924120.7) are already partially able to express well the localization of small tumours based on the rate of counts coming from the areas of interest. The lack of imaging associated to the situation described above, however, does not make it easier for the surgeon to act with absolute certain in identifying the parts to be removed. Also, gamma cameras used in radioimmuno-guided surgery are not so easy to handle as to allow to reach very small zones located between organs, for real-time display of any neoplastic formations and the confirmation of their total elimination after the surgical intervention for their removal.

Object of the present invention is to obtain a veritable miniaturized imaging system sensitive to gamma radiation, of reduced size, usable also for external diagnoses of small tumours (for instance skin melanomas, thyroid exams, etc.), in such a way that the reduced dimensions can allow the total ease of handling of the device which can be held in the palm of a hand, has extremely reduced weight with the ability to display hard to reach areas of interest (between organs). The use of small detectors (areas of roughly 3×3 $cm^2$) able to detect accumulations of radioactivity with the resolution of about 2 mm is therefore applicable in this case.

In the radioisotopic characterization of melanomas, and in general of skin tumour, the use of such high spatial resolution detectors is particularly useful: the suspected lesion is easily identifiable with a physical examination, so the detector can be positioned in the location of the suspected lesion and provide a reception map, with a response that can be roughly predicted as YES/NO.

The same line of reasoning applies to groin or armpit lymph nodes.

The device according to the invention comprises a Position Sensitive Photomultiplier (PSPMT) of the last generation coupled with a scintillation crystal matrix, each element having 2×2 $mm^2$ area (or smaller), a collimator of the same shape and area as the crystals, coupled with suitable electronics for processing the signals from the photo tube and a processing software for real-time visualisation of the areas of interest. The scintillation crystals, all matrix, may be NaI(Tl) or CsI(Tl) or other scintillation crystal.

To attain the purpose, the object has as its subject a miniaturized gamma camera with high spatial resolution, able to be used both during surgical interventions and as an external diagnostic device, with the ability to detect tissue zones invaded by tumours of small area. Additional features and advantages of the invention shall be more readily apparent from the description that follows with reference to the accompanying drawings, provided purely by way of non limiting example, wherein:

FIG. 1a shows the detail of the detection block;

FIG. 2 shows the detail of the collimator;

FIG. 3 shows the scintillating crystal matrix;

FIG. 4 shows the shape of the cladding;

FIG. 8 shows a detail of the operating block diagram of the electronics for the conversion of the pulses from the operational amplifiers;

Figure 1:
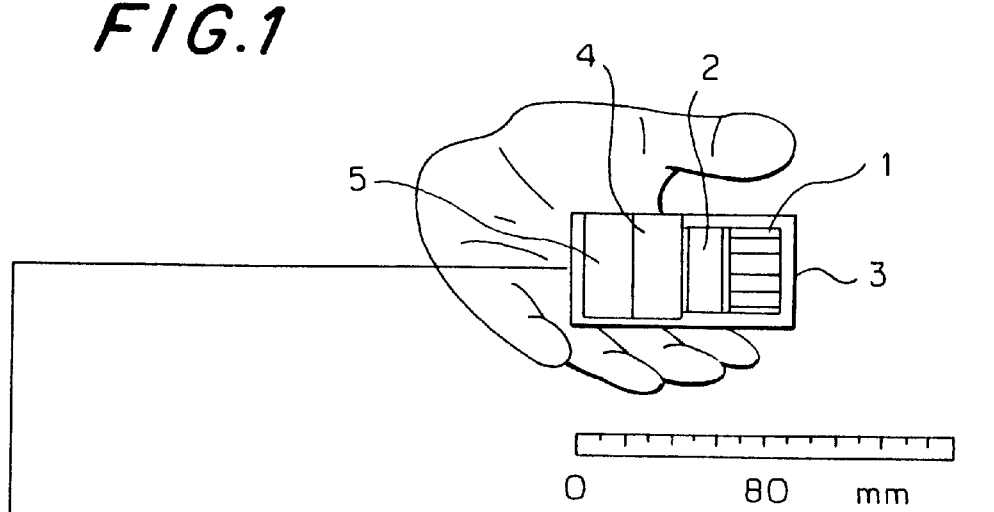
FIG. 1 is an enlarged scale view of the device wherein the parts comprising it are indicated.
Figure 1:
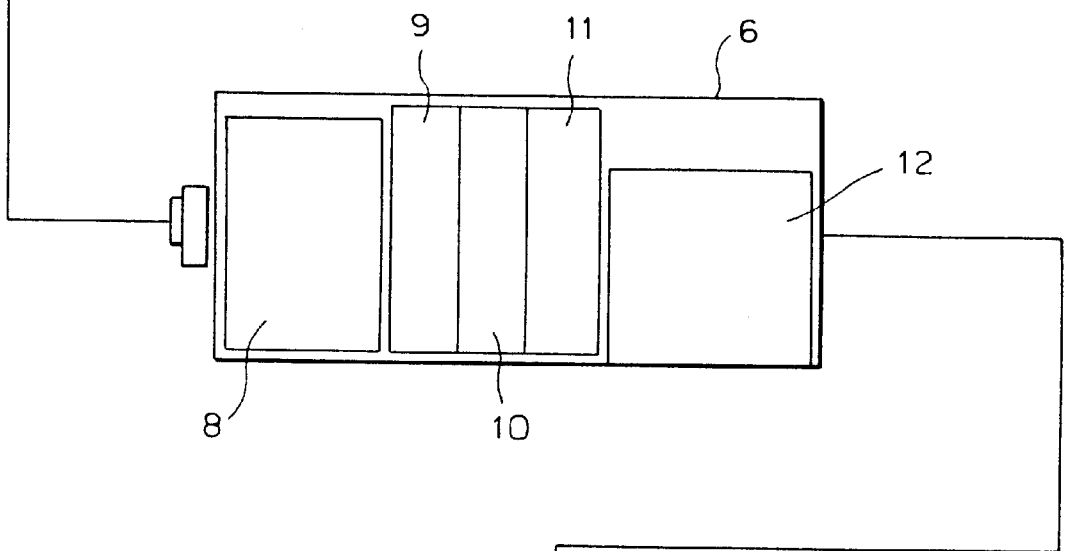
Figure 1:
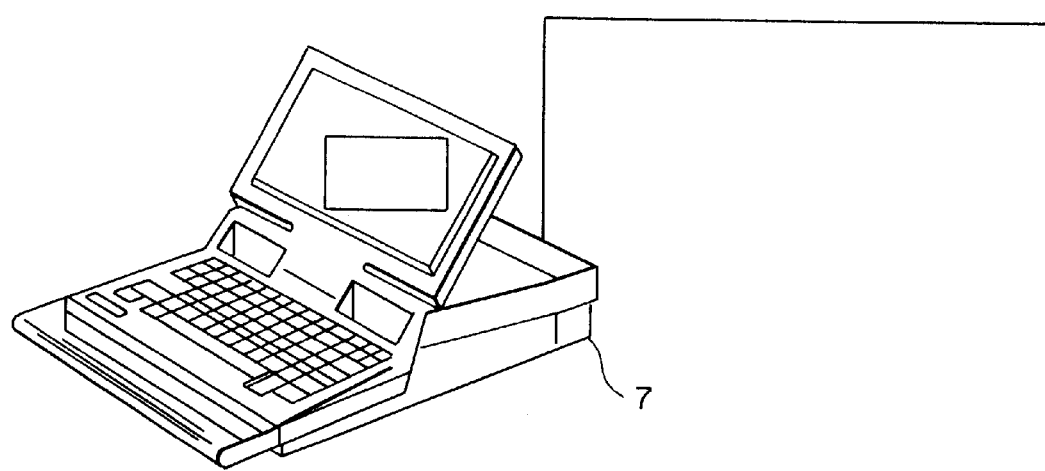
Figure 5:
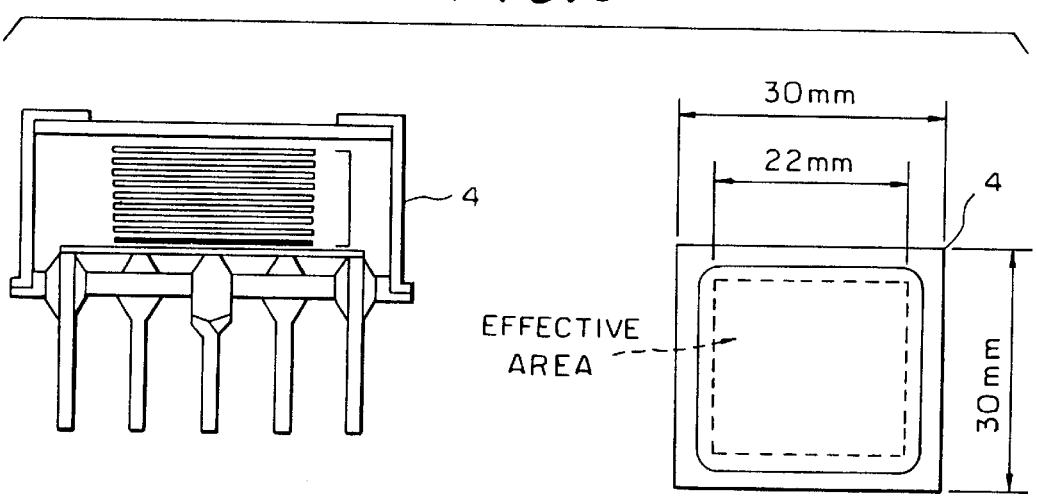
FIG. 5 shows the diagram of the photo multiplier and its dimensions.
Figure 6:
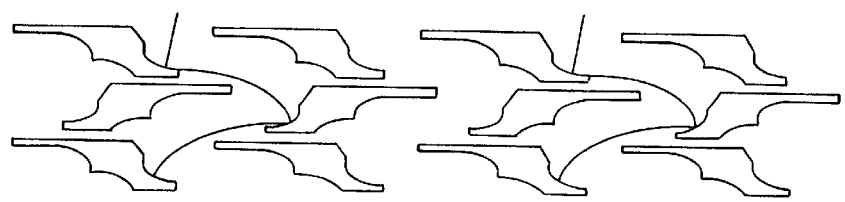
FIG. 6 shows the multiplication mechanism of the electrons in the photo multiplier (metal channel dynodes)
Figure 7:
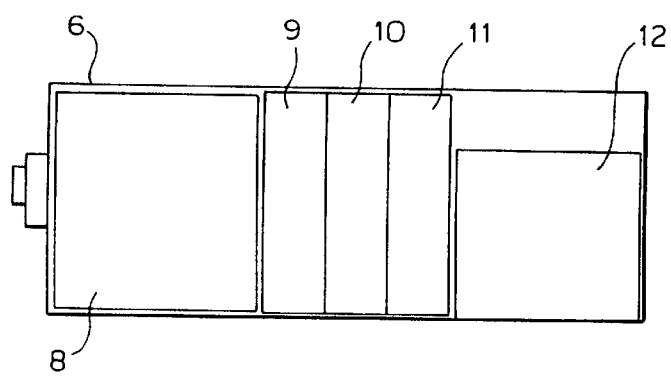
FIG. 7 shows the electronic block diagram required for the operation of the gamma camera.

With reference to the figures, the new gamma camera is shown, comprising:

a collimator 1 made of Lead or high Z metal (such as W, Au, etc.) able to let through only the gamma radiations according to the solid angle crossing through its holes. In a practical embodiment said collimator presents size equal to a parallelepiped with side of 32 mm and height of 30 mm or greater (the three-by-four matrix shown in FIG. 3 is exemplary, and a four-by-four matrix is also within the scope of the present invention, which might for example feed the four-input operational amplifiers of FIGS. 8a and 8b);

a scintillating crystal 2 made of NaI(Tl) (Thallium-doped sodium iodide) sensitive to gamma radiations having energy ranging from a few keV to 1 MeV, with total size equal to a square with side equal to 22 mm or greater;

a cladding 3 constituted by a coating of inert material able to be sterilised for the part to be introduced in the patient, constituted by a parallelepiped with side of 35 mm and length ranging from 50 to 80 mm or more;

a photo multiplier 4, able to collect the optical signal produced by the scintillation crystal and amplified into an electrical signal. Said photo multiplier is of a compact type comprising eleven thin metal channel dynodes encapsulated in a container having total height of about 30 mm, as shown in FIG. 5, and able to be position-sensitive with a multi-anode charge collection system. Subsequently, the eight signals exiting the photo multiplier are sent on eight pre-amplifiers 5. The five, rather than eight, collecting wires shown in FIG. 5 are merely exemplary. A simplified electronics set is used to obtain the sum of the pulses exiting the pre-amplifiers.

Figure 8A:
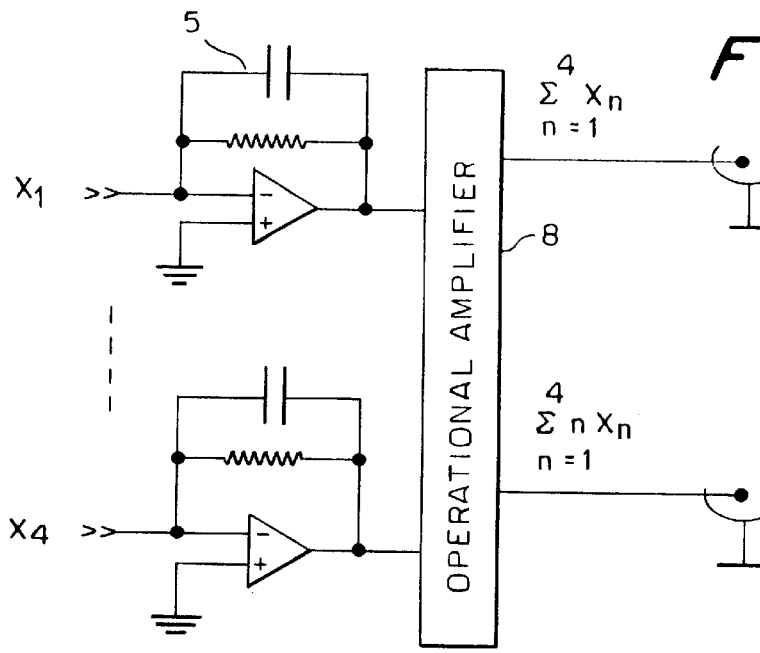
FIGS. 8a and 8b show the operating diagram of the operational amplifiers.
Figure 8B:
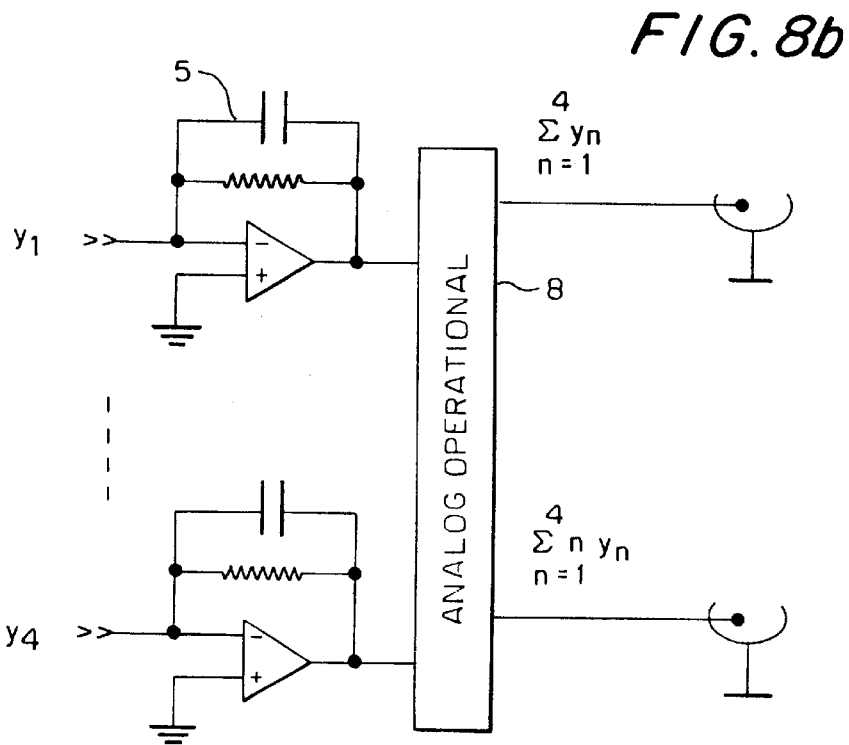
Figure 9:
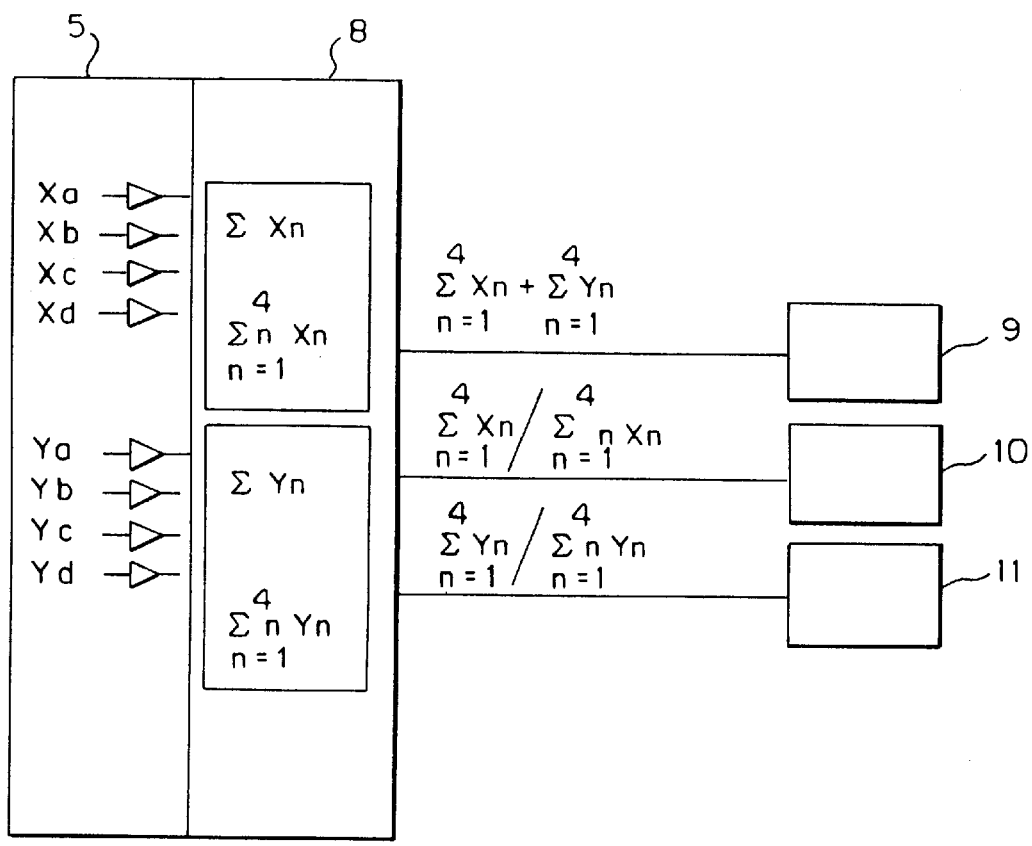
Figure 10:
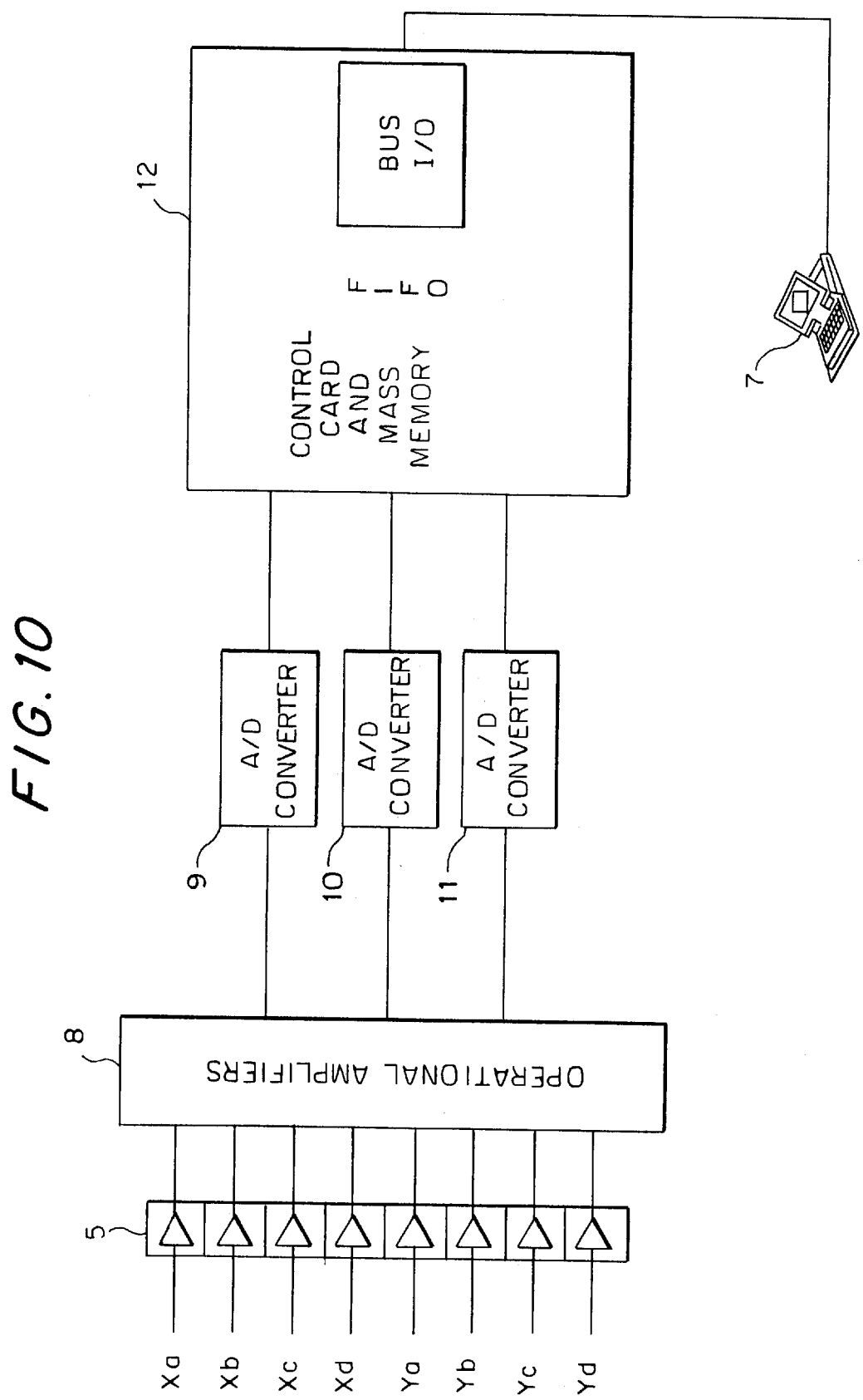
FIG. 10 shows a block diagram of the electronics and of the output signals towards a personal computer.

FIGS. 8a and 8b show a system of eight pre-amplifiers 5 comprising four wire anodes for determining the position on the X axis and four wire anodes for the Y position. The electronic system for reading the charge collected on the anodes is accomplished by means of eight independent pre-amplifiers 5. Subsequently, the pulses are sent to a block of operational amplifiers 8 which perform hardware operations on the input signals. The element 8, as shown in the drawing, accepts the raw signals from the individual collecting wires and performs logical operations on them. The logical operations, in order to produce an image, e.g., intensity, X-coordinate, and Y-coordinate data, are discussed below. These three data are integrated over time in the circuit 8 and output to three A/D converters 9–11 which convert the time-integrated analog signals to digital signals, as shown in FIG. 9. Such integrated data can be fed directly to a personal computer, as is shown in FIG. 10. The symbol on the right side of FIGS. 8a and 8b represents a grounded connector.

In regard to the signal processing mechanism, with reference to FIG. 9, from the operational block 8 exit three signals which subsequently enter three analogue-to-digital converters. In detail, the converter 9 represents the value of the energy of the interacting photon (i.e. the sum of photon-induced charges over X and Y); the converter 10 represents the centroid (or barycenter) for the X co-ordinate of the position of the photon and the converter 11 represents the centroid of the Y co-ordinate of the photon. The subscripts a–d in box 5 of FIG. 9 correspond respectively to the subscripts 1–4 of box 8.

With reference to FIG. 10, the output of the signals from the three converters is sent on a data acquisition control board and sent to a personal computer. The signals related to each co-ordinate of the axes X and Y respectively are connected to an analog operational device which allows simultaneously to perform summing operations of the four signals for X and of the four signals for Y. For the determination of the X co-ordinate and for the Y co-ordinate, the centroid is computed respectively through only two converters. This hardware computation solution for the charge distribution centroid allows to minimise the data to be digitised and transmitted to the computer. The crucial point for data management is the transfer-rate to the computer which for cost reduction reasons shall take place using low-cost, standard computers, operating systems, and interfaces. Moreover, during acquisition the computer shall be able to present the image in "near" real time. In addition to having the capability of determining the position of the incident photon, it shall also be possible to determine its energy by summing the signal exiting the converter 9 which contains the information of the charge released to the scintillation signal. In this way it will be possible to eliminate all those events caused by radiation scattering which are summed on the final image of the exam performed. With an appropriate energy window, it will be possible to correct the image complete with the "background", reducing the noise caused by single or multiple interactions in the body tissue. In this way, the energy window shall discriminate only those photons of a given energy characteristic of the tracer used.

The correction software shall enable real-time displaying of the acquisition of information sent by an appropriate board which is directly connected to the signal converters. The whole gamma camera is coated, with regard to cladding 3, with inert and sterilisable material, as described and, for the remaining part which stavs outside the patient, with a parallelepiped with 35 mm side and length variable between 40 and 80 mm or more.

A suitable presentation software is able to display the information as images of reception of the tracers injected into the patient, with the same representation typical of large-area gamma cameras.

By moving the gamma camera in proximity to the regions of interest in the body of the patient, who has been injected with a radio pharmaceutical product capable of attaching preferably on tumour cells and able to emit gamma radiations of an energy ranging from a few keV to 1 MeV, the surgeon will be able to localize the tumour identifying the area of maximum signal (emission of gamma radiation) with spatial resolution of a few millimeters.

This allows the surgeon to intervene with extreme certainty and precision, only in the specific area involved with the tumour, thereby reducing surgical damage and risk for the patient.

The high sensitivity of the gamma camera, moreover, allows to use radio pharmaceuticals at different energies and it enables to mark specific antibodies for given tumours with different radio isotopes, commonly used in nuclear medicine.

In possible variations of the invention, the miniaturized gamma camera can present, as scintillation crystal, a CsI (Na) crystal matrix, where individual crystals have section of about 1 mm×1 mm and in any case ranging between 0.5 mm×0.5 mm and 3 mm×3 mm and where individual crystals are optically separated from each other, and the separation zone between crystal and crystal has thickness of about 0.1 mm and in any case ranging from 3 microns to 0.5 mm. Moreover, crystals of NaI(Tl), CsI(Tl), SGO, LSO, YAP:Ce, etc., can also be used as scintillating crystals.

In an additional variation, the photo multiplier can be replaced with an analogous one having a greater number of dynodes and a higher number of charge collection anode wires. As a consequence, the electronics are also modifiable by the same principle described above, in proportion to the number of outputs of the photo multiplier.

The dimensions of the photo multiplier used can also be varied, reaching larger dimensions but always such that they can be considered miniaturised with respect to a traditional gamma camera and such as to be usable for the proposed purposes. The principle of the invention is to obtain a device that makes use of a single photo multiplier for the computation of the position of the photons emitted, contrary to gamma cameras of large area which make use of multiple photo multipliers to reach the same purpose.

Total dimensions may change, always remaining extremely reduced and such as to allow the surgeon to move the instrument by hand in a simple and precise manner.

Obviously, moreover, the construction details and the embodiments may be varied widely with respect to what has been described and shown purely by way of example, without thereby departing from the scope of the present invention.

What is claimed is:

1. A miniaturized gamma ray camera system, having very high spatial resolution for the localization of tumors and being usable for external diagnostic and hand-held use during surgical interventions, the system comprising:

(a) a camera comprising:

a gamma-ray collimator (1);

a scintillating crystal (2), producing an optical signal when struck by a gamma ray, the crystal being disposed adjacent one end of the collimator;

a photomultiplier tube (4) adjacent the crystal opposite the gamma-ray collimator, the photomultiplier tube transducing the optical signal into an electrical signal on at least one of a plurality of individual collecting wires, wherein the photomultiplier tube has a cross section of 30 millimeters×30 millimeters and a height not less than 20 millimeters and the plurality of individual collecting wires comprise a multi-anode charge collection system comprising not fewer than four collecting wires for determining an X-position on the X axis and not fewer than four collecting wires for determining a Y-position on the Y axis;

a plurality of signal preamplifiers (5) each connected for amplifying the signal on a respective one of the collecting wires; and cladding (3) around the collimator, crystal, photomultiplier tube, and preamplifiers; and (b) an electronic device (6) coupled to the camera and comprising a hard-wired circuit (8) comprising operational amplifiers, the circuit accepting a respective signal from each signal preamplifier and outputting three signals to three converters respectively, the three signals comprising:

(1) a first signal representing a time integration of gamma-ray energy deposited on the scintillating crystal energy, which first signal is coupled to a first analog-to-digital converter (9);

(2) a second signal representing an X co-ordinate, which second signal is coupled to a second analog-to-digital converter (10); and (3) a third signal representing a Y co-ordinate, which third signal is coupled to a third analog-to-digital converter (11);

whereby an output of the three converters is connectable to a computer including appropriate software to display gamma radiation images imaged by the camera.

2. The miniaturized gamma camera according to claim 1, wherein the collimator has a cross section between 6 and 10 millimeter and a length between 5 and 30 millimeter.

3. The miniaturized gamma camera according to claim 1, wherein the scintillating crystal comprises a matrix of individual crystals having cross section between 0.5 and 3 millimeter and wherein the individual crystals are optically separated from each other by a separation zone having thickness in the range from 3 microns to 0.5 millimeter.

4. The miniaturized gamma camera according to claim 1, wherein the cladding includes a coating of inert material able to be sterilized.

5. The miniaturized gamma camera according to claim 1, wherein the scintillating crystal and the photomultiplier are optically coupled by optical fibers of inorganic material.

6. The miniaturized gamma camera according to claim 1, wherein the time integration includes a summation $$\Sigma^4_{n=1}X_n + \Sigma^4_{n=1}Y_n.$$

7. The miniaturized gamma camera according to claim 1, wherein the X-coordinate includes a quotient $$\Sigma^4_{n=1}X_n / \Sigma^4_{n=1}nX_n.$$

8. The miniaturized gamma camera according to claim 1, wherein the Y-coordinate includes a quotient $$\Sigma^4_{n=1}Y_n / \Sigma^4_{n=1}nY_n.$$

* * * * *